United States Patent
Pinkos et al.

(10) Patent No.: US 10,450,252 B2
(45) Date of Patent: Oct. 22, 2019

(54) METHOD FOR HYDROGENATING CARBOXYLIC ACIDS IN ORDER TO FORM ALCOHOLS

(71) Applicant: BASF SE, Ludwigshafen am Rhein (DE)

(72) Inventors: Rolf Pinkos, Ludwigshafen am Rhein (DE); Stefan Rittinger, Ludwigshafen am Rhein (DE); Christoph Nuebling, Ludwigshafen am Rhein (DE); Olivier Abillard, Ludwigshafen am Rhein (DE)

(73) Assignee: BASF SE, Ludwigshafen am Rhein (DE)

(*) Notice: Subject to any disclaimer, the term of this patent is extended or adjusted under 35 U.S.C. 154(b) by 0 days.

(21) Appl. No.: 16/089,495

(22) PCT Filed: Mar. 29, 2017

(86) PCT No.: PCT/EP2017/057350
§ 371 (c)(1),
(2) Date: Sep. 28, 2018

(87) PCT Pub. No.: WO2017/167772
PCT Pub. Date: Oct. 5, 2017

(65) Prior Publication Data
US 2019/0112245 A1    Apr. 18, 2019

(30) Foreign Application Priority Data
Mar. 31, 2016 (EP) .................................. 16163203

(51) Int. Cl.
*C07C 29/149* (2006.01)
*C07C 29/17* (2006.01)

(52) U.S. Cl.
CPC .......... *C07C 29/149* (2013.01); *C07C 29/177* (2013.01)

(58) Field of Classification Search
CPC ............................. C07C 29/149; C07C 29/177
See application file for complete search history.

(56) References Cited

U.S. PATENT DOCUMENTS

| | | | |
|---|---|---|---|
| 3,478,112 A | 11/1969 | Adam et al. | |
| 4,940,805 A | 7/1990 | Fischer et al. | |
| 5,698,749 A | 12/1997 | Pedersen et al. | |
| 8,383,866 B2 * | 2/2013 | Pinkos | C07C 29/149 |
| | | | 568/864 |
| 9,556,136 B2 | 1/2017 | Rittinger et al. | |
| 10,077,223 B2 | 9/2018 | Duefert et al. | |
| 2003/0114719 A1 | 6/2003 | Fischer et al. | |
| 2011/0124926 A1 | 5/2011 | Pinkos et al. | |
| 2018/0002303 A1 | 1/2018 | Duefert et al. | |

FOREIGN PATENT DOCUMENTS

| | | |
|---|---|---|
| DE | 2321101 A1 | 11/1974 |
| WO | WO-2016008904 A1 | 1/2016 |
| WO | WO-2016026726 A1 | 2/2016 |
| WO | WO-20160110520 A1 | 7/2016 |

OTHER PUBLICATIONS

International Search Report for PCT/EP2017/057350 dated Jul. 27, 2017.
Written Opinion of the International Searching Authority for PCT/EP2017/057350 dated Jul. 27, 2017.

* cited by examiner

*Primary Examiner* — Rosalynd A Keys
(74) *Attorney, Agent, or Firm* — Drinker Biddle & Reath LLP

(57) ABSTRACT

Process for the continuous hydrogenation of a carboxylic acid (I) to an alcohol (II) by means of hydrogen at a temperature of from 100 to 300° C. and a pressure of 10 to 33 MPa abs in a reactor tube through which axial flow occurs and which has a fixed-bed catalyst which is fixed therein and comprises at least one element from the group consisting of Re, Co and Cu, and in which the carboxylic acid (I) to be hydrogenated is present in a liquid mixture (III) comprising the carboxylic acid (I), water and alcohol (II), where the mixture (III) has an acid number of from 0.2 to 25 mg KOH/g and comprises at least 15% by weight of water and at least 20% by weight of alcohol (II) and the flow velocity of the flowing liquid calculated on the basis of the geometric cross-sectional area of the empty, catalyst-free reactor tube is from 10 to 50 m/h.

11 Claims, No Drawings

METHOD FOR HYDROGENATING CARBOXYLIC ACIDS IN ORDER TO FORM ALCOHOLS

CROSS-REFERENCE TO RELATED APPLICATIONS

This application is a national stage application (under 35 U.S.C. § 371) of PCT/EP2017/057350, filed Mar. 29, 2017, which claims benefit of European Application No. 16163203.9, filed Mar. 31, 2016, both of which are incorporated herein by reference in their entirety.

The present invention relates to a process for the continuous hydrogenation of a carboxylic acid of the general formula (I)

$$Y^1—X^1—COOH \tag{I}$$

where $X^1$ is a —$(CH_2)_n$— group with n from 1 to 10 or a —CH=CH— group and $Y^1$ is H—, HOOC— or HO—$CH_2$-, or a mixture thereof, with retention of the number of carbon atoms to give an alcohol of the general formula (II)

$$Y^2—X^2—CH_2OH \tag{II}$$

where $X^2$ is a —$(CH_2)_n$- group with n from 1 to 10 and $Y^2$ is H— or HO—$CH_2$—, by means of hydrogen at a temperature of from 100 to 300° C. and a pressure of from 10 to 33 MPa abs in a reactor tube through which axial flow occurs and which has a fixed-bed catalyst which is fixed therein and comprises at least one element from the group consisting of Re, Co and Cu.

Alcohols are an important class of compounds having a wide use spectrum. Thus, they are used, for example, as solvents or as intermediate in the synthesis of high-value compounds. A possible synthesis route for many alcohols is catalytic oxidation of hydrocarbons to carboxylic acids and subsequent catalytic hydrogenation of these. 1,4-Butanediol is thus obtained industrially by oxidation of n-butane to maleic anhydride, the hydrolysis of this to form maleic acid and/or esterification thereof to form dialkyl maleate and subsequent hydrogenation, with succinic acid and 4-hydroxybutyric acid being formed as intermediates. 1,6-Hexanediol is prepared industrially by hydrogenation of adipic acid and also 6-hydroxycaproic acid, with both acids being obtained as by-product in the industrial oxidation of cyclohexane to cyclohexanone and cyclohexanol. In addition, adipic acid is also obtained as pure material by nitric acid oxidation of cyclohexanol. 1,4-Butanediol and 1,6-hexanediol are important intermediates in the preparation of polymers.

U.S. Pat. No. 5,698,749 describes the preparation of 1,4-butanediol by hydrogenation of maleic acid, maleic anhydride, fumaric acid, succinic acid, succinic anhydride, dimethyl succinate or gamma-butyrolactone as starting material over a catalyst comprising a catalyst comprising at least one element from the group consisting of Re, W and Mo. The hydrogenation is carried out batchwise in an autoclave or continuously in a fixed-bed reactor in a single pass using a relatively highly concentrated aqueous solution having a content of starting material of up to 50% by weight. A disadvantage of this mode of operation is the residual content of unreacted carboxylic acid, which leads both to a reduced yield of desired product and also, owing to the residual acid, to disadvantages in the product quality.

U.S. Pat. No. 3,478,112 describes the hydrogenation of carboxylic acids to the corresponding alcohols over a catalyst comprising Co and also at least one element from the group consisting of Cu, Cr and Mn. The carboxylic acid to be hydrogenated can also be used as aqueous solution. Furthermore, the US patent teaches the use of a carboxylic acid solution diluted by product alcohol. The hydrogenation is carried out batchwise in an autoclave or continuously in a fixed-bed reactor in a single pass.

Despite the dilution of the carboxylic acid to be used as taught in U.S. Pat. No. 3,478,112, the carboxylic acid content of the starting solution is relatively high in the range from about 25 to 50% by weight of carboxylic acid estimated from the examples. Accordingly, the disadvantages of a reduced yield of desired product and also a reduced product quality due to the residual acid present as mentioned in the acknowledgement of U.S. Pat. No. 5,698,749 also apply to the process according to U.S. Pat. No. 3,478,112.

US 2011/0,124,926 teaches the preparation of dials by hydrogenation of corresponding carboxylic acids, carboxylic anhydrides or lactones over a Co-comprising fixed-bed catalyst with introduction of alkali metal ions or alkaline earth metal ions. The carboxylic acid to be hydrogenated can be used as pure substance or as a solution in, for example, water or an alcohol. Despite the corresponding dilution, the acid content of the carboxylic acid solution is relatively high and is, for example in example 1, more than 36% by weight. In order to remove the heat evolved in the hydrogenation, the US document teaches the partial recirculation of the hydrogenation output.

A disadvantage of this mode of operation is the relatively high content of unreacted carboxylic acid in the reactor output, which leads to a reduced yield of desired product and also to reduced product quality due to the residual acid present. Thus, example 2 discloses, in the hydrogenation of a mixture comprising adipic acid and 6-hydroxycaproic acid with addition of NaOH, a reactor output which comprises from 1.4 to 2.3% by weight of 6-hydroxycaproic acid in addition to from 27 to 28% by weight of 1,6-hexanediol.

DE 2,321,101 discloses the hydrogenation of carboxylic acids to the corresponding alcohols over a catalyst comprising Co, Cu and Mn and also Mo. The hydrogenation is carried out over a catalyst fixed bed or in suspension in aqueous and/or alcoholic solution. The DE first publication also teaches the use of product alcohol as diluent.

Despite the dilution of the carboxylic acid to be used as taught in DE 2,321,101 and the partial recirculation of the hydrogenated mixture as mentioned in example 1a, the carboxylic acid content of the reactor feed is relatively high. Thus, the feed mixture in example 1a has an acid number of 62 mg KOH/g and the reactor output has an acid number of 1.8 mg KOH/g. Significant amounts of unhydrogenated residual acid are thus present in the reactor output. Accordingly, the disadvantages of a reduced yield of desired product and also a reduced product quality due to the residual acid present as mentioned in the acknowledgement of U.S. Pat. No. 5,698,749 also apply to the process according to DE 2,321,101.

U.S. Pat. No. 4,940,805 discloses the preparation of 1,4-butanediol, tetrahydrofuran and gamma-butyrolactone by hydrogenation of maleic acid or succinic acid or anhydrides and esters thereof over a catalyst comprising Cu and also at least one element from the group consisting of Cu, P and Mo. The starting material to be hydrogenated can be present as a melt or be dissolved in alcohol and additionally comprise water. Continuous hydrogenation over a catalyst fixed bed in the downflow mode or upflow mode with partial recirculation of the hydrogenation output is mentioned as preferred mode of operation.

Thus, example 1 in U.S. Pat. No. 4,940,805 describes the hydrogenation of an aqueous solution comprising 40% by weight of maleic acid over a fixed-bed catalyst comprising $H_3PO_4$, CoO, CuO, $Mn_3O_4$ and $MoO_3$ in the downflow mode with a fresh input of the solution mentioned of 200 g/h and a recirculation rate of 9 l/h. Under these conditions, a yield of 1,4-butanediol of only from 29.6 to 38.8%, based on the maleic acid used, was achieved.

A disadvantage of the process described in U.S. Pat. No. 4,940,805 is the formation of a mixture comprising considerable amounts of tetrahydrofuran and gamma-butyrolactone and thus the associated low yield of 1,4-butanediol.

It was an object of the present invention to find a process for the continuous hydrogenation of saturated or unsaturated carboxylic acids to the corresponding alcohols, which does not have the abovementioned disadvantages, or has them only to a greatly reduced extent, and makes possible, in particular, virtually complete hydrogenation of the carboxylic acids to the corresponding alcohols with simultaneous avoidance of appreciable overhydrogenation of the alcohols. Correspondingly, the new process should have a high carboxylic acid conversion at a high selectivity to the corresponding alcohols. In addition, the process should be technically simple to carry out and be suitable for the after-hydrogenation of a stream which still comprises carboxylic acids from the industrial preparation of diols, for example 1,4-butanediol or 1,6-hexanediol, which stream was obtained by prehydrogenation of relatively highly concentrated carboxylic acid solutions.

We have surprisingly found a process for the continuous hydrogenation of a carboxylic acid of the general formula (I)

$$Y^1—X^1—COOH \qquad (I)$$

where $X^1$ is a —$(CH_2)_n$— group with n from 1 to 10 or a —CH=CH— group and $Y^1$ is H—, HOOC— or HO—$CH_2$—, or a mixture thereof, with retention of the number of carbon atoms to give an alcohol of the general formula (II)

$$Y^2—X^2—CH_2OH \qquad (II)$$

where $X^2$ is a —$(CH_2)_n$— group with n from 1 to 10 and $Y^2$ is H— or HO—$CH_2$—, by means of hydrogen at a temperature of from 100 to 300° C. and a pressure of from 10 to 33 MPa abs in a reactor tube through which axial flow occurs and which has a fixed-bed catalyst which is fixed therein and comprises at least one element from the group consisting of Re, Co and Cu, and wherein the carboxylic acid (I) to be hydrogenated is present in a liquid mixture (III) comprising the carboxylic acid (I), water and alcohol (II), where the mixture (III)

a) has an acid number of from 0.2 to 25 mg KOH/g,
b) comprises at least 15% by weight of water,
c) comprises at least 20% by weight of alcohol (II) and
d) the flow velocity of the flowing liquid calculated on the basis of the geometric cross-sectional area of the empty, catalyst-free reactor tube is from 10 to 50 m/h.

The starting material for the process of the invention is a mixture (III) comprising the carboxylic acid (I) to be hydrogenated, water and alcohol (II).

The carboxylic acid (I) is a carboxylic acid of the general formula (I)

$$Y^1—X^1—COOH \qquad (I)$$

where $X^1$ is a —$(CH_2)_n$— group with n from 1 to 10 or a —CH=CH— group and $Y^1$ is H—, HOOC— or HO—$CH_2$—. Specifically, the group of the carboxylic acid (I) to be hydrogenated comprises $CH_3$—COOH (acetic acid),
$CH_3$—$(CH_2)_2$—COOH (propionic acid),
$CH_3$—$(CH_2)_2$—COOH (butyric acid),
$CH_3$—$(CH_2)_3$—COOH (valeric acid),
$CH_3$—$(CH_2)_4$—COOH (caproic acid),
$CH_3$—$(CH_2)_5$—COOH (enanthic acid),
$CH_3$—$(CH_2)_6$—COOH (caprylic acid),
$CH_3$—$(CH_2)_7$—COOH (pelargonic acid),
$CH_3$—$(CH_2)_8$—COOH (capric acid),
$CH_3$—$(CH_2)_9$—COOH (undecanoic acid),
$CH_2$=CH—COOH (acrylic acid),
HOOC—$CH_2$—COOH (malonic acid),
HOOC—$(CH_2)_2$—COOH (succinic acid),
HOOC—$(CH_2)_3$—COOH (glutaric acid),
HOOC—$(CH_2)_4$—COOH (adipic acid),
HOOC—$(CH_2)_5$—COOH (pimelic acid),
HOOC—$(CH_2)_6$—COOH (suberic acid),
HOOC—$(CH_2)_7$—COOH (azelaic acid),
HOOC—$(CH_2)_8$—COOH (sebacic acid),
HOOC—$(CH_2)_9$—COOH (undecanedioic acid),
HOOC—$(CH_2)_{10}$—COOH (dodecanedioic acid),
cis HOOC—CH=CH—COOH (maleic acid),
trans HOOC—CH=CH—COOH (fumaric acid),
HO—$CH_2$—$CH_2$—COOH (3-hydroxypropionic acid),
HO—$CH_2$—$(CH_2)_2$—COOH (4-hydroxybutyric acid),
HO—$CH_2$—$(CH_2)_3$—COOH (5-hydroxyvaleric acid),
HO—$CH_2$—$(CH_2)_4$—COOH (6-hydroxycaproic acid),
HO—$CH_2$—$(CH_2)_5$—COOH (7-hydroxyenanthic acid),
HO—$CH_2$—$(CH_2)_6$—COOH (8-hydroxycaprylic acid),
HO—$CH_2$—$(CH_2)_7$—COOH (9-hydroxypelargonic acid),
HO—$CH_2$—$(CH_2)_8$—COOH (10-hydroxycapric acid),
HO—$CH_2$—$(CH_2)_9$—COOH (11-hydroxyundecanoic acid),
HO—$CH_2$—$(CH_2)_{10}$—COOH (12-hydroxydodecanoic acid),
cis HO—$CH_2$—CH=CH—COOH (4-hydroxyisocrotonic acid) and
trans HO—$CH_2$—CH=CH—COOH (4-hydroxycrotonic acid).

Naturally, mixtures of the carboxylic acids mentioned are also possible.

$X^1$ is preferably a —$(CH_2)_n$— group with n from 1 to 4 or a —CH=CH— group. Among the carboxylic acids (I) preferred here, special preference is given to acetic acid, succinic acid, 4-hydroxybutyric acid, maleic acid, fumaric acid, glutaric acid, 5-hydroxyvaleric acid, adipic acid, 6-hydroxycaproic acid and mixtures thereof.

$X^1$ is particularly preferably a —$(CH_2)_n$— group with n from 2 to 4 or a —CH=CH— group. Independently thereof, $Y^1$ is particularly preferably a HOOC— or HO—$CH_2$— group. Taking into account the particularly preferred groups for $X^1$ and $Y^1$, the carboxylic acid (I) to be hydrogenated is succinic acid, 4-hydroxybutyric acid, maleic acid, fumaric acid, glutaric acid, 5-hydroxyvaleric acid, adipic acid, 6-hydroxycaproic acid or a mixture thereof.

Very particular preference is given to succinic acid, 4-hydroxybutyric acid, maleic acid, glutaric acid, 5-hydroxyvaleric acid, adipic acid, 6-hydroxycaproic acid and mixtures thereof, in particular succinic acid, 4-hydroxybutyric acid, maleic acid, adipic acid, 6-hydroxycaproic acid and mixtures thereof.

The carboxylic acid (I) mentioned is catalytically hydrogenated with retention of the number of carbon atoms to give an alcohol of the general formula (II)

$$Y^2—X^2—CH_2OH \qquad (II)$$

where $X^2$ is a —$(CH_2)_n$— group with n from 1 to 10 and $Y^2$ is H— or HO—$CH_2$—. As a result of the hydrogenation, a —$CH_2OH$ group is in each case formed from the —COOH groups. If the carboxylic acid (I) additionally comprises a —CH═CH— group, a —$CH_2$—$CH_2$— group is formed therefrom.

Corresponding to the carboxylic acid (I) used, $X^2$ of the alcohol (II) formed therefrom is preferably a —$(CH_2)_n$— group with n from 1 to 4. Among the alcohols preferred as a result, special preference is given to ethanol, 1,4-butanediol, 1,5-pentanediol, 1,6-hexanediol and mixtures thereof.

$X^2$ is particularly preferably a —$(CH_2)_n$— group with n from 2 to 4. Independently thereof, $Y^2$ is particularly preferably a HO—$CH_2$—. group. Taking into account the particularly preferred groups for $X^2$ and $Y^2$, the alcohols (II) are 1,4-butanediol, 1,5-pentanediol, 1,6-hexanediol and mixtures thereof, in particular 1,4-butanediol, 1,6-hexanediol and mixtures thereof.

Thus, for example, succinic acid, 4-hydroxybutyric acid, maleic acid and fumaric acid are hydrogenated to 1,4-butanediol, glutaric acid and 5-hydroxyvaleric acid are hydrogenated to 1,5-pentanediol and adipic acid and 6-hydroxycaproic acid is hydrogenated to 1,6-hexanediol.

As mentioned above, virtually complete hydrogenation of the carboxylic acids to the corresponding alcohols with simultaneous avoidance of appreciable overhydrogenation of the alcohols is desirable. It has surprisingly been found that this objective is achieved when a liquid mixture (III) comprising the carboxylic acid (I), water and alcohol (II) is used, where the mixture (III)

a) has an acid number of from 0.2 to 25 mg KOH/g,
b) comprises at least 15% by weight of water and
c) comprises at least 20% by weight of alcohol (II),
the hydrogenation is carried out at a temperature of from 100 to 300° C. and a pressure of from 10 to 33 MPa abs in a reactor tube through which axial flow occurs and which has a fixed-bed catalyst which is fixed therein and comprises at least one element from the group consisting of Re, Co and Cu and
d) the flow velocity of the flowing liquid calculated on the basis of the geometric cross-sectional area of the empty, catalyst-free reactor tube is from 10 to 50 m/h.

The content of the carboxylic acid (I) to be hydrogenated is defined by the acid number of the mixture (III). The acid number is a chemical parameter for characterizing acidic constituents in mixtures. It is the mass of potassium hydroxide in mg which is necessary to neutralize the acids comprised in 1 g of the mixture. The acid number is determined by (i) mixing 1.5 g of the mixture to be examined at a temperature of 20° C. with 10 ml of pyridine, 50 ml of tetrahydrofuran, 5 ml of water and 10 drops of a solution comprising 0.1% by weight of phenolphthalein in ethanol,
(ii) titrating the mixture with a solution comprising 0.1 mol % of potassium hydroxide in ethanol,
(iii) determining the amount of potassium hydroxide added until the end point from colorless to pink is attained and
(iv) conversion of the amount of potassium hydroxide determined to the unit mg KOH per g of mixture.

In the process of the invention, the acid number of the mixture (III) to be hydrogenated is from 0.2 to 25 mg KOH/g. The amount of carboxylic acid (I) corresponding to this range is dependent on the molar mass of the carboxylic acid and also on the number of acid groups. Thus, in the case of a mixture comprising water, alcohol and the monobasic carboxylic acid 6-hydroxycaproic acid (molar mass 132.16 g/mol), this range corresponds to a content of from 0.047 to 5.89% by weight of 6-hydroxycaproic acid. In the case of a corresponding mixture comprising the dibasic succinic acid, this range corresponds to a content of from 0.021 to 2.63% by weight of succinic acid.

The acid number of the mixture (III) to be hydrogenated is preferably ≥0.5 mg KOH/g and particularly preferably ≥1 mg KOH/g, and preferably ≤20 mg KOH/g, particularly preferably ≤15 mg KOH/g and very particularly preferably ≤10 mg KOH/g.

The content of water in the mixture (III) to be used is at least 15% by weight and not more than 80% by weight minus the amount of carboxylic acid (I) comprised in the mixture (III). The content of water is preferably at least 20% by weight, particularly preferably at least 30% by weight and very particularly preferably at least 50% by weight.

The content of alcohol (II) in the mixture (III) to be used is at least 20% by weight and not more than 85% by weight minus the amount of carboxylic acid (I) comprised in the mixture (III). The content of alcohol (II) is preferably at least 25% by weight, particularly preferably at least 30% by weight and very particularly preferably at least 45% by weight.

The sum of the contents of water and alcohol (II) in the mixture (III) to be used is preferably at least 60% by weight and particularly preferably at least 85% by weight.

Apart from the carboxylic acid (I) to be hydrogenated, water and alcohol (I), the mixture (III) to be used can comprise further components in different amounts. Thus, the sum of the contents of carboxylic acid (I), water and alcohol (II) in the mixture (III) is ≤100% by weight. If the mixture (III) does not comprise any further components, the sum mentioned is 100% by weight. If the mixture (III) comprises further components, the sum mentioned is <100% by weight. The sum of the contents of carboxylic acid (I), water and alcohol (II) in the mixture (III) is preferably from 40 to 100% by weight.

The mixture (III) to be used in the process of the invention can be of various origins. Thus, it is possible, for example, to produce the mixture (III) by mixing the individual components. However, it is also possible and generally even advantageous to obtain the mixture (III) by catalytic prehydrogenation of a solution comprising the carboxylic acid (I) and water. In this prehydrogenation, the carboxylic acid (I) is first and foremost hydrogenated to the alcohol (II) but a certain residual amount of carboxylic acid (I) remains, so that the mixture obtained comprises carboxylic acid (I), water and alcohol (II).

As reactors, apparatuses which comprise one or more parallel reactor tubes are used in the process of the invention. The reactor tubes are characterized by a cross-sectional area CSA in a length L. In general, the ratio of the length to the square root of the cross-sectional area is such that $$1 \leq L/\sqrt{CSA} \leq 1000.$$

$L/\sqrt{CSA}$ is preferably ≥2, particularly preferably ≥5 and very particularly preferably ≥10, and preferably ≤750, particularly preferably ≤500 and very particularly preferably ≤100. If a plurality of reactor tubes are connected in series, the abovementioned ratio is calculated by adding up the lengths and the average of the length-weighted cross-sectional areas is used. The absolute length, or in the case of reactor tubes connected in series, the total length thereof, is usually from 0.5 m to 50 m, preferably ≥1 m, particularly preferably ≥4 m, and preferably ≤8 m and particularly preferably ≤10 m.

As examples of suitable reactors, mention may be made of shaft reactors and shell-and-tube reactors. Shell- and tube reactors use a plurality of parallel reactor tubes. Even though just two reactor tubes connected in parallel by definition form a shell-and-tube reactor, the usual number of parallel tubes in a shell-and-tube reactor is from 50 to 22 000.

The reactor tubes are usually oriented vertically. Flow through them occurs axially and the liquid mixture (III) can be passed through them either in the upflow mode, i.e. from the bottom upward, or in the downflow mode, i.e. from the top downward. The gaseous hydrogen can be introduced either in cocurrent or in countercurrent. The hydrogen is preferably introduced in cocurrent.

In the process of the invention, a fixed-bed catalyst which is fixed in the reactor tube is used as hydrogenation catalyst. The fixing of the fixed-bed catalyst is usually effected by methods known to those skilled in the art. Thus, the fixed-bed catalyst can, for example, rest on a support tray or on a bed of inert balls, for instance steatite balls.

The fixed-bed catalyst to be used in the process of the invention comprises at least one element from the group consisting of rhenium (Re), cobalt (Co) and copper (Cu). Preference is given to catalysts which comprise one element from the group consisting of Re and Co. In principle, the catalysts can comprise further metallic and nonmetallic elements in addition to the elements mentioned.

The fixed-bed catalyst to be used can be produced in various ways using conventional technical knowledge. Thus, the fixed-bed catalyst can, for example, be produced by steeping or impregnation of a support, by precipitation on a support, by precipitation of the entire material or by other methods known to those skilled in the art.

When an Re-comprising fixed-bed catalyst is used, this generally comprises from 0.1 to 10% by weight of Re, based on the reduced fixed-bed catalyst. Apart from Re, the catalyst can optionally comprise further metals as catalytically active components. Examples which may be mentioned are Pd, Ru, Pt, Sn, Co, Cu and Fe. If further metals are used as catalytically active components, the content thereof is usually in the range from traces to 15% by weight, based on the reduced fixed-bed catalyst.

The Re-comprising fixed-bed catalysts are preferably supported catalysts. These are preferably produced by steeping or impregnation of suitable supports in/with suitable Re salts or by precipitation of suitable Re salts on a suitable support. Suitable and at the same time preferred supports are carbons, for example graphite or activated carbon, $ZrO_2$, $Al_2O_3$, $SiO_2$, $TiO_2$ or mixtures thereof, and also compounds thereof with zeolites or clays. Activated carbon is particularly preferred as support. The supports can be used either as prefabricated shaped bodies or else, for example, in powder form for steeping, impregnation or precipitation. As Re salts suitable for steeping, impregnation or precipitation, mention may be made by way of example of $NH_4ReO_4$ or $Re_2O_7$, which are, for example, present in the form of an aqueous solution. In the case of precipitation, the Re salts, which are, for example, present as aqueous solution, are reduced by means of reducing substances such as hydrogen or hydrazine and Re is thus precipitated on. The catalyst precursor obtained is subsequently usually dried. Drying is preferably carried out at from 80 to 150° C., particularly preferably from 100 to 130° C. If a pulverulent support has been used, shaping, for example by tableting, is carried out after drying. Appropriate methods for producing Re-comprising supported catalysts, including the further processing to give the ready-to-use fixed-bed catalyst, are known to those skilled in the art. The production of Re-comprising fixed-bed catalysts is described, for example, in US 2003/0,114,719 and the references cited therein.

The Co- or Cu-comprising fixed-bed catalysts are preferably precipitated catalysts. However, they can also be produced by steeping, impregnation or other methods known to those skilled in the art.

In the case of a Co-comprising fixed-bed catalyst, this generally comprises from 1 to 90% by weight, preferably from 10 to 85% by weight and particularly preferably from 25 to 80% by weight, of Co, based on the reduced fixed-bed catalyst. A solution of a suitable Co salt is used for precipitation. Suitable Co salts are, for example, $Co(NO_3)_2$, Co acetate or Co chloride. These are usually dissolved in water and form an acidic solution having a pH of <7. To carry out the precipitation, the solution is generally placed in a mixed vessel, for example a stirred vessel, and a suitable basic solution is introduced as precipitant to increase the pH. A suitable basic solution is, for example, an aqueous $Na_2CO_3$ solution (soda solution). As a result, the pH increases and the basic Co salt formed precipitates. In the case of a soda solution as precipitant, Co carbonate, for example, is formed.

In the case of a Cu-comprising fixed-bed catalyst, this generally comprises from 0.5 to 60% by weight, preferably from 2 to 55% by weight and particularly preferably from 5 to 50% by weight, of Cu, based on the reduced fixed-bed catalyst. The precipitation of a Cu-comprising fixed-bed catalyst is carried out in a manner similar to that in the case of a Co-comprising fixed-bed catalyst. Suitable Cu salts are, for example, $Cu(NO_3)_2$, Cu acetate or Cu chloride. These are usually dissolved in water and form an acidic solution having a pH of <7. To carry out the precipitation, the solution is generally placed in a mixed vessel, for example a stirred vessel, and a suitable basic solution is introduced as precipitant to increase the pH. A suitable basic solution is, for example, an aqueous $Na_2CO_3$ solution (soda solution). As a result, the pH increases and the basic Cu salt formed precipitates. In the case of a soda solution as precipitant, Cu carbonate, for example, is formed.

It is also possible and may be advantageous to precipitate the Co salt and Cu salt together in a manner analogous to the above description in order to produce a Co- and Cu-comprising fixed-bed catalyst. In addition, it may also be possible to precipitate further metal salts together with Co and/or Cu salts from suitable solutions. As further metals, mention may be made by way of example of Mo, Ti, Zr, Sn or Mn. In the case of Mo, Ti, Zr, Sn and Mn, aqueous solutions of the nitrates are also suitable starting materials here.

In order to complete the precipitation, it is generally advantageous to leave the freshly precipitated suspension for some time, for example from 10 minutes to 24 hours, preferably from 1 to 5 hours, while mixing further and if the pH drops to below pH 6 to introduce further basic precipitant.

The suspension obtained is subsequently filtered and the solid is washed, for example with water, and dried. Drying is preferably carried out at from 80 to 150° C., particularly preferably from 100 to 130° C. In order to obtain the oxides, the dried filtercake is subsequently calcined in a stream of air. Calcination is preferably carried out at from 250 to 700° C., particularly preferably from 300 to 600° C. and very particularly preferably from 400 to 600° C. The calcination time is usually from 0.1 to 10 hours, preferably from 0.3 to 5 hours.

To effect shaping, the calcined oxide is mixed with water or an aqueous solution and kneaded. As aqueous solutions suitable for mixing to form a paste, mention may be made by way of example of ammoniacal solutions of promotor metals. The kneaded composition is subsequently extruded in an extruder to give extrudates. The extrudates obtained are dried and subsequently calcined. Drying is preferably carried out at from 80 to 150° C., particularly preferably from 100 to 130° C. Calcination is preferably carried out at from 300 to 700° C. and particularly preferably from 400 to 600° C.

As an alternative to shaping by extrusion, it is also possible to tablet the calcined oxide. For this purpose, the calcined oxide is generally admixed with tableting aids such as graphite powder or Cu powder and shaped to give pellets.

Furthermore, the fixed-bed catalyst can also comprise alkali metals and alkaline earth metals, usually in ionic form. Explicit mention may be made here of Na, K, Mg and Ca. The total content of alkali metals and alkaline earth metals is generally from 0 to 5% by weight and preferably from 0 to 2% by weight, based on the reduced fixed-bed catalyst. The presence of alkali metals and alkaline earth metals is particularly advantageous in the case of Co- or Cu-comprising fixed-bed catalysts. In the case of Co- or Cu-comprising precipitated catalysts, the addition of the alkali metals and alkaline earth metals is usually effected by addition of a solution comprising alkali metals or alkaline earth metals during the precipitation. Ideally, the alkali metals or alkaline earth metals are introduced via the precipitant. Thus, for example, the use of a soda solution leads to the precipitated catalyst subsequently comprising Na.

In a preferred embodiment of the process of the invention, a fixed-bed catalyst comprising from 30 to 85% by weight of Co and from 0.1 to 2% by weight of Na and/or K, based on the reduced fixed-bed catalyst, is used.

The production of Co- or Cu-comprising fixed-bed catalysts is described, for example, in DE-A 23 21 101.

In the process of the invention, preference is given to using
- a supported catalyst comprising from 0.1 to 10% by weight of Re on a support from the group comprising graphite, activated carbon, $ZrO_2$, $Al_2O_3$, $SiO_2$ and $TiO_2$,
- a precipitated catalyst comprising from 1 to 90% by weight of Co,
- a precipitated catalyst comprising from 0.5 to 60% by weight of Cu or
- a precipitated catalyst comprising from 15 to 85% by weight of Co and from 5 to 20% by weight of Cu, where the sum of the contents of Co and Cu does not exceed 100% by weight, in each case based on the reduced fixed-bed catalyst.

The Re-, Co- and/or Cu-comprising fixed-bed catalyst to be used in the process of the invention generally consists of shaped bodies. Use is normally made of shaped bodies of the same type and of the same size. However, it is also possible to use mixtures of various types of shaped bodies and sizes of shaped bodies. Suitable types of shaped bodies are, in particular, pellets, spheres and extrudates, with the cross-sectional shape also being able to deviate from a solid circle. Thus, for example, star-shaped pellets or extrudates and also hollow spaces which run all the way through, for instance in the case of pellets having a hole, are possible. Preference is given to pellets and rod-shaped bodies. The dimensions of the shaped bodies are generally in the range from 2 mm to 5 cm. In the case of pellets, spheres and extrudates, the preferred diameter is from 2 to 10 mm. In the case of pellets, the height thereof is preferably from 2 to 6 mm. In the case of extrudates, the length thereof is preferably from 3 to 20 mm.

The Re-, Co- and/or Cu-comprising fixed-bed catalyst is preferably activated by means of hydrogen before being used in the catalytic hydrogenation of the carboxylic acid (I). The activation can be carried out within or outside the hydrogenation reactor. If it is carried out outside the hydrogenation reactor, the fixed-bed catalyst is for this purpose usually installed in a tube which allows hydrogen to be passed through. In the case of an Re-comprising fixed-bed catalyst, the activation is advantageously carried out at a temperature of from 200 to 350° C. and a pressure of from 0.1 to 1 MPa abs by passing hydrogen through for a period of from 0.5 to 24 hours. In the case of a Co- and/or Cu-comprising fixed-bed catalyst, the activation is advantageously carried out at a temperature of from 130 to 330° C. and a pressure of from 0.1 to 1 MPa abs by passing hydrogen through for a period of from 3 to 72 hours. If the fixed-bed catalyst has been activated outside the hydrogenation reactor, it should be passivated by carefully passing an oxidizing gas, preferably a nitrogen- and oxygen-comprising stream, through it before it is transferred into the hydrogenation reactor. Methods of activating and passivating Re- or Co- and/or Cu-comprising fixed-bed catalysts are generally known to those skilled in the art.

The hydrogen to be used in the process of the invention can be fed in either undiluted or in diluted form with inert gas, for example nitrogen. The introduction of a hydrogen-comprising gas having a very high content of hydrogen is advantageous. Preference is given to a content of hydrogen of ≥80% by volume, particularly preferably ≥90% by volume and very particularly preferably ≥95% by volume.

The amount of hydrogen to be used should be such that at least a small part remains unconsumed at the reactor outlet. The amount of hydrogen fed in is preferably such that ≥5%, particularly preferably ≥10% and very particularly preferably ≥15%, of the hydrogen introduced remains unconsumed at the reactor outlet. Preference is given to ≤90% and particularly preferably ≤80% of the amount of hydrogen introduced being present at the reactor outlet.

The process of the invention is carried out at a temperature of from 100 to 300° C., preferably ≥130° C. and particularly preferably ≥150° C., and preferably ≤250° C. and particularly preferably ≤240° C. The pressure is from 10 to 33 MPa abs, preferably ≥15 MPa abs and particularly preferably ≥20 MPa abs, and preferably ≤30 MPa abs and particularly preferably ≤28 MPa abs.

An important feature of the invention is the provision of a flow velocity of the flowing liquid calculated on the basis of the geometric cross-sectional area of the empty, catalyst-free reactor tube of from 10 to 50 m/h, Only by means of this surprising measure is virtually complete hydrogenation of the carboxylic acids to the corresponding alcohols achieved while at the same time avoiding appreciable overhydrogenation of the alcohols.

The flow velocity of the flowing liquid calculated on the basis of the geometric cross-sectional area of the empty, catalyst-free reactor tube is the calculated ratio v (in m/h) of the volume flow of the flowing liquid V (in m³/h) to the geometric cross-sectional area of the empty, catalyst-free reactor tube CSA (in m²)

$$v = \frac{\dot{V}}{CSA}.$$

The geometric cross-sectional area of the empty, catalyst-free reactor tube CSA as calculated parameter is independent of the amount and geometry of the fixed-bed catalyst used. For instance, a reactor tube having the internal diameter ID has the geometric cross-sectional area $$CSA = \left(\frac{ID}{2}\right)^2 \pi.$$

If the flow velocity of the flowing liquid calculated on the basis of the geometric cross-sectional area of the empty, catalyst-free reactor tube increases to values above 50 m/h, the residual content of carboxylic acids in the hydrogenation output increases. Virtually complete hydrogenation of the carboxylic acids to the corresponding alcohols is thus no longer achieved. The desired alcohol is therefore still contaminated with the undesirable carboxylic acids. If the flow velocity of the flowing liquid calculated on the basis of the geometric cross-sectional area of the empty, catalyst-free reactor tube drops to values below 10 m/h, the content of the desired alcohol also decreases as a result of overhydrogenation or ether formation. The consequence is ultimately a loss of desired product and a reduction in the yield.

The flow velocity of the flowing liquid calculated on the basis of the geometric cross-sectional area of the empty, catalyst-free reactor tube is preferably ≥15 m/h and particularly preferably ≥20 m/h, and preferably ≤45 m/h and particularly preferably ≤40 m/h.

The space velocity over the catalyst in the process of the invention is generally in the range from 0.1 to 50 m³ of liquid mixture (III) per m³ of bed volume of the fixed-bed catalyst used and hour, or in abbreviated form from 0.1 to 50 m³/m³ h. The space velocity over the catalyst is preferably ≥0.5 m³/m³ h and particularly preferably ≥1 m³/m³ h, and preferably ≤20 m³/m³ h and particularly preferably ≤10 m³/m³ h.

Since the evolution of heat in the hydrogenation is likewise relatively low because of the relatively low acid number of the liquid mixture (III) of from 0.2 to 25 mg KOH/g, cooling of the reactor is not necessary, even though it is naturally also possible to use cooled reactors. The hydrogenation according to the invention is usually carried out adiabatically. The adiabatic temperature increase is usually in the range from 1 to 30° C., preferably in the range from 1.5 to 20° C. and particularly preferably in the range from 2 to 10° C.

The process of the invention can be carried out either with or without recirculation of hydrogenated mixture. If the process is carried out with recirculation, up to 75% by weight and optionally up to 50% by weight of the hydrogenated mixture is generally added to the mixture (III) to be hydrogenated. Apart from an increase in the volume flow of the liquid to be passed through the reactor, the concentration of the carboxylic acid (I) to be hydrogenated is also decreased by the recirculation. Correspondingly, the adiabatic temperature in the case of an adiabatic mode of operation thus also decreases. Since this is relatively low even without recirculation because of the relatively low acid number of the liquid mixture (III), recirculation can generally be dispensed with.

For this reason, the process of the invention is preferably carried out without recirculation of hydrogenated mixture.

As mentioned above in the description of the fixed-bed catalyst, this catalyst can also comprise alkali metals and alkaline earth metals. Alkali metals and alkaline earth metals have a selectivity-increasing effect. They promote the desired hydrogenation of the carboxylic acid (I) to the alcohols (II) and reduce the undesirable overhydrogenation of the alcohols. However, the fixed-bed catalyst loses alkali metal ions and/or alkaline earth metal ions during the hydrogenation as a result of bleeding. To counter this effect and ensure a high selectivity during operation, it is advantageous to introduce alkali metals or alkaline earth metals in the form of salts which are soluble in the mixture (III) during operation. Since sodium and potassium are particularly readily available, the introduction of these metals in the form of their corresponding salts is preferred. However, the $pK_a$ of the corresponding acid of these salts should be less than the $pK_a$ of formic acid. Particular preference is given to introducing the particularly readily available hydroxides or carboxylates of Na or K.

The mixture (III) to be hydrogenated preferably comprises from 10 to 1000 ppm by weight of alkali metals or alkaline earth metals, particularly preferably ≥20 ppm by weight, in particular ≥50 ppm by weight, and particularly preferably ≤500 ppm by weight, in particular ≤400 ppm by weight.

In a particularly preferred embodiment, the mixture (III) comprises from 10 to 1000 ppm by weight of alkali metal from the group consisting of Na and K.

The hydrogenation according to the invention gives a hydrogenated mixture having an acid number which is significantly lower than that of the mixture (III) used. Even when a mixture (III) having an original acid number of 25 mg KOH/g is used, a hydrogenated mixture having an acid number of <0.5 mg KOH/g is possible.

The desired alcohols (II) can, for example, subsequently be isolated from the hydrogenated mixture. The isolation can generally be carried out according to normal knowledge in the art, for example by distillation. In this way, the desired alcohols (II) can be obtained in high purity. Purities of ≥99% by weight and preferably ≥99.5% by weight are thus possible.

As mentioned above, it is possible and generally even necessary to obtain the mixture (III) to be hydrogenated in the process of the invention by catalytic prehydrogenation of a solution comprising the carboxylic acid (I) and water. Such solutions are formed, for example, as intermediate in the targeted preparation of the alcohols (II). Thus, for example, 1,4-butanediol can be obtained by hydrogenation of maleic acid, which is in turn obtained according to known methods by catalytic oxidation of n-butane to maleic anhydride and subsequent hydrolysis. 1,5-Pentanediol can, for example, be obtained by hydrogenation of glutaric acid or 5-hydroxyvaleric acid, which are in turn obtainable by oxidation of cyclopentanone. 1,6-Hexanediol can, for example, be obtained by hydrogenation of adipic acid or 6-hydroxycaproic acid, which are obtained as by-products in the catalytic oxidation of cyclohexane to cyclohexanone and cyclohexanol. Such solutions obtained by oxidation comprise the corresponding carboxylic acids (I) in sometimes high concentrations. The acid number of such solutions is thus usually in the range from 50 to 900 mg KOH/g, preferably in the range from 100 to 900 mg KOH/g. The abovementioned solutions can be hydrogenated by processes known to those skilled in the art. Appropriate processes are, for example, carried out continuously in the presence of a heterogeneous hydrogenation catalyst. Suitable hydrogenation catalysts comprise, for example, one or more elements from groups 7 to 11 of the Periodic Table, preferably Re, Ru, Co, Pd, Pt, Cu. Suitable processes have, for example, been described in US 2011/0,124,926 or U.S. Pat. No. 5,698,749.

Although the carboxylic acid (I) is hydrogenated first and foremost to the alcohol (II) in these hydrogenations, a certain residual amount of carboxylic acid (I) remains, so that the mixture obtained usually comprises carboxylic acid (I), water and alcohol (II) and has a composition like that of the mixture (III).

For this reason, the mixture (III) to be hydrogenated is, in a preferred embodiment of the process of the invention, obtained by continuous prehydrogenation of a solution comprising carboxylic acid (I) and water, with the solution having an acid number of from 50 to 900 mg KOH/g.

Due to the relatively high acid number, the heat liberated in the prehydrogenation is also relatively high. It is therefore advantageous to carry out the prehydrogenation with recirculation of the prehydrogenated solution to obtain better removal of heat. It is advantageous to recirculate from 50 to 98% by weight of the prehydrogenated solution back to the prehydrogenation.

In a preferred embodiment for the hydrogenation of succinic acid to 1,4-butanediol, a mixture (III) which comprises succinic acid, water and 1,4-butanediol and has an acid number of from 0.2 to 10 mg KOH/g and comprises at least 15% by weight of water and at least 20% by weight of 1,4-butanediol is hydrogenated in a single pass without recirculation at a temperature of from 130 to 250° C. and a pressure of from 15 to 28 MPa abs in the presence of a fixed-bed catalyst comprising Re, Co and/or Cu in a reactor tube through which axial flow occurs at a flow velocity of the flowing liquid calculated on the basis of the geometric cross-sectional area of the empty, catalyst-free reactor tube of from 10 to 50 m/h and in the presence of from 10 to 1000 ppm by weight of Na ions. The mixture (III) to be used in the hydrogenation according to the invention is preferably produced by prehydrogenation of a solution which comprises maleic acid and has an acid number in the range from 100 to 900 mg KOH/g over a fixed-bed catalyst comprising Re, Ru, Co, Pd, Pt and/or Cu, with the prehydrogenation being carried out with recirculation of from 50 to 98% by weight of the prehydrogenated solution. The mixture obtained from the hydrogenation according to the invention comprises only traces of succinic acid and has an acid number of <0.5 mg KOH/g.

In a preferred embodiment for the hydrogenation of 6-hydroxycaproic acid and adipic acid to 1,6-hexanediol, a mixture (III) which comprises 6-hydroxycaproic acid, adipic acid, water and 1,6-hexanediol and has an acid number of from 0.2 to 10 mg KOH/g and comprises at least 15% by weight of water and at least 20% by weight of 1,6-hexanediol is hydrogenated in a single pass without recirculation at a temperature of from 130 to 250° C. and a pressure of from 15 to 28 MPa abs in the presence of a fixed-bed catalyst comprising Re, Co and/or Cu in a reactor tube through which axial flow occurs at a flow velocity of the flowing liquid calculated on the basis of the geometric cross-sectional area of the empty, catalyst-free reactor tube of from 10 to 50 m/h and in the presence of from 10 to 1000 ppm by weight of Na ions. The mixture (III) to be used in the hydrogenation according to the invention is preferably produced by prehydrogenation of a solution which comprises 6-hydroxycaproic acid and adipic acid and has an acid number in the range from 100 to 900 mg KOH/g over a fixed-bed catalyst comprising Re, Ru, Co, Pd, Pt and/or Cu, with the prehydrogenation being carried out with recirculation of from 50 to 98% by weight of the prehydrogenated solution. The mixture obtained from the hydrogenation according to the invention comprises only traces of 6-hydroxycaproic acid and adipic acid and has an acid number of <0.5 mg KOH/g.

The process of the invention makes the continuous hydrogenation of saturated and unsaturated carboxylic acids to the corresponding alcohols with virtually complete hydrogenation of the carboxylic acids to the corresponding alcohols and simultaneous avoidance of appreciable overhydrogenation of the alcohols possible. It makes it possible to obtain a high carboxylic acid conversion with high selectivity to the corresponding alcohols. In addition, it is technically simple to carry out. The process is particularly suitable for the after-hydrogenation of a stream still comprising carboxylic acids from the industrial preparation of dials, for example 1,4-butanediol or 1,6-hexanediol, which has been obtained by prehydrogenation of relatively highly concentrated carboxylic acid solutions.

EXAMPLES

Examples 1 to 4 (Hydrogenation of Succinic Acid to 1,4-Butanediol)

Production of an Re/Pd Catalyst
(5% of Re, 5% of Pd on Oxidized Activated Carbon)

500 g of activated carbon having a particle size of 30×70 mesh were in each case admixed with an excess (supernatant solution) of concentrated nitric acid (69-71% strength $HNO_3$) and stirred at 80° C. for about 18 hours. After cooling, the product was isolated by filtration, washed a number of times with an excess of water and dried at 120° C.

1.5 kg of the oxidized activated carbon produced as described above were in each case then mixed with 7.2 kg of an aqueous solution comprising 114 g of $NH_4ReO_4$ and 1.09 kg of an aqueous $Pd(NO_3)_2$ solution having a Pd content of 7.26% by weight and the slurry obtained was evaporated to dryness and subsequently dried at 120° C. and tableted to give 3×3 mm pellets.

Production of a Prehydrogenated Feed by Hydrogenation of Maleic Acid 3.00 liters of the Re/Pd catalyst pellets produced by the abovementioned method were then introduced into a 10 m long reactor tube having an internal diameter of 2 cm and firstly activated therein. For this purpose, the catalyst was heated in a stream of hydrogen at 1° C. per minute to 200° C. and then kept in the stream of nitrogen at 200° C. for 5 hours.

A stream of 0.5 kg/h of a 33% strength by weight solution of maleic acid in water was then hydrogenated continuously over this catalyst at 20 MPa abs, from 150 to 170° C. and a product recirculation rate of 5 kg/h with introduction of 250 standard l/h of hydrogen and the reaction output was collected. After 4 weeks of continuous operation, the process was stopped and the collected reaction output was analyzed.

The feed which had been prehydrogenated in this way had a water content of about 75% by weight. As organic components, it comprised, according to gas-chromatographic analysis, calculated on a water-free basis, about 90.7% by weight of 1,4-butanediol, about 2.4% by weight of tetrahydrofuran, about 2.5% by weight of n-butanol, about 0.5% by weight of gamma-butyrolactone and also further reaction products of maleic acid. The acid number of the prehydrogenated feed was 3.8 mg KOH/g and was predominantly attributable to succinic acid.

Hydrogenation of Succinic Acid in the Prehydrogenated Feed to 1,4-Butanediol

To carry out the hydrogenation of the succinic acid, 3.00 liters of the Re/Pd catalyst pellets produced by the above-mentioned method were introduced into a 10 m long reactor tube having an internal diameter of 2 cm and firstly activated. For this purpose, the catalyst was heated in a stream of hydrogen at 1° C. per minute to 200° C. and then kept in the stream of hydrogen at 200° C. for 5 hours.

The prehydrogenated feed was subsequently passed continuously in the downflow mode over the catalyst at a reactor inlet temperature of 170° C., 20 MPa abs together with 70 standard l/h of hydrogen per kg of prehydrogenated feed. In the present trial, the amount of prehydrogenated feed fed in was gradually increased, with sampling being carried out in each case about 24 hours after setting of an inflow amount.

The results are shown in table 1. The water content was determined by the Karl-Fischer method and the content of 1,4-butanediol was determined gas-chromatographically.

Examples 1 to 4 show the dependence of the acid number and also of the content of target alcohol on the flow velocity of the liquid in the tube reactor.

At a low flow velocity of only 5 m/h (example 1), the carboxylic acid present is hydrogenated largely completely, which is shown by a very low acid number of <0.5 mg KOH/g, but appreciable amounts of the target alcohol 1,4-butanediol are also destroyed by hydrogenation.

Thus, the content of 1,4-butanediol decreases from an original 90.7% by weight to 88.0% by weight, in each case calculated on a water-free basis.

A high flow velocity of 60 m/h (example 4) does give a high calculated throughput through the reactor, but allows only partial hydrogenation of the carboxylic acid present. Thus, the output still has an acid number of 1.5 mg KOH/g, which corresponds to hydrogenation of only about 60% of the carboxylic acid present.

In comparison, examples 2 and 3 with a flow velocity of 10 and 30 m/h, respectively, show both virtually complete hydrogenation of the carboxylic acid present, as indicated by an acid number in the output of <0.5 mg KOH/g, and also a significant increase in the target alcohol 1,4-butanediol, as indicated by a significantly increased content of 1,4-butanediol of 94.5 and 94.3% by weight, respectively.

The hydrogenation according to the invention gave a virtually carboxylic acid-free product stream with a significant increase in target alcohol from a feed stream comprising alcohol and carboxylic acid.

Examples 5 to 8 (Hydrogenation of 6-Hydroxycaproic Acid to 1,6-Hexanediol)

Production of a Co/Cu/Mn/Mo Catalyst (66% of CoO, 20% of CuO, 7.3% of $Mn_3O_4$, 3.6% of $MoO_3$, 0.15% of $Na_2O$, 3% of $H_3PO_4$)

The Co/Cu/Mn catalyst precursor was produced by two-stage precipitation of a starting mixture composed of 38.3 kg of an aqueous cobalt nitrate solution comprising 12.6% by weight of cobalt, 6.53 kg of an aqueous copper nitrate solution comprising 15.3% by weight of copper, 2.78 kg of an aqueous manganese nitrate solution comprising 12.6% by weight of manganese and 0.199 kg of 75.3% strength by weight phosphoric acid with 20% strength by weight soda solution. Starting mixture was fed continuously in an amount corresponding to 1.5 kg of metal oxide/h into a first stirred vessel (useful capacity 6 l) at 50° C. and admixed while stirring with the amount of soda solution required to maintain a pH of 8.5 (measured using a glass electrode). The incomplete precipitation mixture is transferred in its entirety into a second vessel and then after-precipitated at a pH of from 6.5 to 7.5 (optionally with addition of further soda solution) over a period of 2 hours. The suspension obtained was filtered and the solid was washed and dried.

This gave a basic carbonate having a BET surface area of about 120 $m^2$/g. This carbonate was then decomposed to the oxide at a temperature in the range from 420 to 540° C. in a stream of air and washed free of residual alkali with deionized water. 4 kg of the washed and dried oxide were then admixed in a kneader with 652 g of an ammoniacal Mo solution which had been produced by dissolution of technical-grade molybdenum oxide hydrate in aqueous ammonia solution and had a calculated $MoO_3$ content of 25.5% by weight and mixed by kneading. During kneading, the phosphorus discharged by means of the washing processes was replaced by fresh phosphoric acid and 285 g of a 65.3% strength by weight nitric acid and 1300 g of deionized water were introduced and the mixture was kneaded intensively for 2.5 hours. The kneaded composition was then shaped to give extrudates having a diameter of 4 mm and a length of from 3 to 9 mm, dried, and calcined at 500° C. for 6 hours. The extrudates had a bulk density of 1700 g/l.

Hydrogenation of 6-Hydroxycaproic Acid to 1,6-Hexanediol 3.00 liters of the Co/Cu/Mn/Mo catalyst described were then introduced into a 10 m long reactor tube having an internal diameter of 2 cm. The feed to be hydrogenated was obtained by prehydrogenation of a mixture which comprises 17% by weight of adipic acid, 16% by weight of 6-hydroxycaproic acid, 2% by weight of glutaric acid, 1.5% by weight of 5-hydroxypentanoic acid, 1% by weight of formic acid, 1% by weight of 1,4-cyclohexanediol, 1% by weight of 1,2-cyclohexanediol and 0.3% by weight of cyclohexanol/cyclohexanone and is formed as by-product in the oxidation of cyclohexane to cyclohexanol/cyclohexanone and has been obtained by scrubbing with water over a Co/Cu/Mn/Mo catalyst as described above. The prehydrogenated feed had a water content of about 52.5% by weight. As organic components, it comprised, according to gas-chromatographic analysis, calculated on a water-free basis, 61.1% by weight of 1,6-hexanediol and further reaction products of the abovementioned by-product stream. The acid number of the prehydrogenated feed was 6.5 mg KOH/g and was predominantly attributable to 6-hydroxycaproic acid and traces of adipic acid. Further components in the prehydrogenated feed were, inter alia, 1-hexanol, 1-pentanol, 1,2-cyclohexanediol, 1,3-cyclohexanediol, 1,4-cyclohexanediol, 1,5-pentanediol, 1-pentanol and 1,4-butanediol.

To carry out the hydrogenation of the 6-hydroxycaproic acid and of the adipic acid, the prehydrogenated feed was passed continuously in the downflow mode over the catalyst at a reactor inlet temperature of 230° C., 25 MPa abs together with 50 standard liters/h of hydrogen per kg of prehydrogenated feed. In the present trial, the amount of prehydrogenated feed fed in was gradually increased, with sampling being carried out in each case about 24 hours after setting of an inflow amount.

The results are shown in table 2. The water content was determined by the Karl-Fischer method and the content of 1,4-butanediol was determined gas-chromatographically.

At a low flow velocity of only 5 m/h (example 5), the carboxylic acids present are hydrogenated largely completely, which is indicated by a very low acid number of <0.5 mg KOH/g, but appreciable amounts of the target alcohol 1,6-hexanediol are also destroyed by hydrogenation. Thus, the content of 1,6-hexanediol decreases from an original 61.1% by weight to 60.2% by weight, in each case calculated on a water-free basis.

A high flow velocity of 60 m/h (example 8) does give a high calculated throughput through the reactor but allows only partial hydrogenation of the carboxylic acids present. Thus, the output still has an acid number of 2.3 mg KOH/g, which corresponds to hydrogenation of only about 65% of the carboxylic acids present.

In comparison, examples 6 and 7 with a flow velocity of 10 and 30 m/h, respectively, show virtually complete hydrogenation of the carboxylic acids present, as indicated by an acid number in the output of <0.5 mg KOH/g, and also a significant increase in target alcohol 1,6-hexanediol, as indicated by a significantly increased content of 1,6-hexanediol of 64.0 and 64.1% by weight, respectively.

A virtually carboxylic acid-free product stream with a significant increase in target alcohol was obtained by the hydrogenation according to the invention from a feed stream comprising alcohol and carboxylic acid.

Example 9

In example 9 (comparative example), the long-term behavior of the hydrogenation of 6-hydroxycaproic acid to 1,6-hexanediol at a flow velocity of the flowing liquid calculated on the basis of the geometric cross-sectional area of the empty, catalyst-free reactor tube of 60 m/h was examined. For this purpose, example 8 was firstly repeated and left under these conditions for a period of 1000 hours. During this time, the acid number in the output slowly increased from 2.3 to 4.5 mg KOH/g. Correspondingly, the carboxylic acid conversion decreased from about 65 to about 30%. At the same time, small amounts of Co and Mn totaling up to 10 ppm by weight were found in the output.

Comparative example 9 shows a tremendous deterioration in the performance within only 1000 hours, Example 10

In example 10, the long-term behavior of the hydrogenation of 6-hydroxycaproic acid to 1,6-hexanediol at a flow velocity of the flowing liquid calculated on the basis of the geometric cross-sectional area of the empty, catalyst-free reactor tube of 30 m/h was examined. For this purpose, example 7 was firstly repeated and left under these conditions for a period of 3000 hours. During this time, the acid number in the output slowly increased from <0.5 to just 0.6 mg KOH/g. The carboxylic acid conversion after 3000 hours was thus still above 90%. Co and Mn were detected in only a small total amount of <4 ppm by weight.

Example 10 shows only a slight increase in the acid number and in the Co and Mn content in the output even after 3000 hours of operation at a flow velocity of 30 m/h.

TABLE 1

| | | Cross-sectional | Feed | | | Output | | |
|---|---|---|---|---|---|---|---|---|
| Example | Feed [l/h] | throughput [#1] [m/h] | Acid number [mg KOH/g] | 1,4-BDO [#2] [% by wt] | Water [% by wt] | Acid number [mg KOH/g] | 1,4-BDO [#2] [% by wt] | Water [% by wt] |
| 1 (comparison) | 1.6 | 5 | 3.8 | 90.7 | 75.0 | <0.5 | 88.0 | 75.5 |
| 2 (invention) | 3.1 | 10 | | | | <0.5 | 94.5 | 75.2 |
| 3 (invention) | 9.4 | 30 | | | | <0.5 | 94.3 | 75.1 |
| 4 (comparison) | 19 | 60 | | | | 1.5 | 93.0 | 75.1 |

[#1] Flow velocity of the flowing liquid calculated on the basis of the geometric cross-sectional area of the empty, catalyst-free reactor tube.
[#2] 1,4-Butanediol, calculated on a water-free basis.

TABLE 2

| | | Cross-sectional | Feed | | | Output | | |
|---|---|---|---|---|---|---|---|---|
| Example | Feed [l/h] | throughput [#1] [m/h] | Acid number [mg KOH/g] | 1,6-HDO [#2] [% by wt] | Water [% by wt] | Acid number [mg KOH/g] | 1,6-HDO [#2] [% by wt] | Water [% by wt] |
| 5 (comparison) | 1.6 | 5 | 6.5 | 61.1 | 52.5 | <0.5 | 60.2 | 53.5 |
| 6 (invention) | 3.1 | 10 | | | | <0.5 | 64.0 | 53.0 |
| 7 (invention) | 9.4 | 30 | | | | <0.5 | 64.1 | 52.9 |
| 8 (comparison) | 19 | 60 | | | | 2.3 | 61.0 | 52.7 |

[#1] Flow velocity of the flowing liquid calculated on the basis of the geometric cross-sectional area of the empty, catalyst-free reactor tube.
[#2] 1,6-Hexanediol, calculated on a water-free basis.

The invention claimed is:

1. A process for the continuous hydrogenation of a carboxylic acid of the general formula (I)

$$Y^1\text{—}X^1\text{—}COOH \qquad (I)$$

where $X^1$ is a —$(CH_2)_n$— group with n from 1 to 10 or a —CH=CH— group and $Y^1$ is H—, HOOC— or HO—$CH_2$—, or a mixture thereof, with retention of the number of carbon atoms to give an alcohol of the general formula (II)

$$Y^2\text{—}X^2\text{—}CH_2OH \qquad (II)$$

where $X^2$ is a —$(CH_2)_n$- group with n from 1 to 10 and $Y^2$ is H— or HO—$CH_2$—, by means of hydrogen at a temperature of from 100 to 300° C. and a pressure of from 10 to 33 MPa abs in a reactor tube through which axial flow occurs and which has a fixed-bed catalyst which is fixed therein and comprises at least one element from the group consisting of Re, Co and Cu, wherein the carboxylic acid (I) to be hydrogenated is present in a liquid mixture (III) comprising the carboxylic acid (I), water and alcohol (II), where the mixture (III)
  a) has an acid number of from 0.2 to 25 mg KOH/g,
  b) comprises at least 15% by weight of water,
  c) comprises at least 20% by weight of alcohol (II) and
  d) the flow velocity of the flowing liquid calculated on the basis of the geometric cross-sectional area of the empty, catalyst-free reactor tube is from 10 to 50 m/h.

2. The process according to claim 1, wherein the mixture (III) has an acid number of from 0.5 to 10 mg KOH/g.

3. The process according to claim 1, wherein the sum of the contents of carboxylic acid (I), water and alcohol (II) in the mixture (III) is ≤100% by weight.

4. The process according to claim 3, wherein the sum of the contents of carboxylic acid (I), water and alcohol (II) in the mixture (III) is from 40 to 100% by weight.

5. The process according to claim 1, wherein the flow velocity of the flowing liquid calculated on the basis of the geometric cross-sectional area of the empty, catalyst-free reactor tube is 20-40 m/h.

6. The process according to claim 1, wherein the process is carried out without recirculation of hydrogenated mixture.

7. The process according to claim 1, wherein the mixture (III) comprises from 10 to 1000 ppm by weight of alkali metal selected from the group consisting of Na and K.

8. The process according to claim 1, wherein succinic acid, 4-hydroxybutyric acid, maleic acid, glutaric acid, 5-hydroxyvaleric acid, adipic acid, 6-hydroxycaproic acid or a mixture thereof is used as carboxylic acid (I).

9. The process according to claim 1, wherein
  a supported catalyst comprising from 0.1 to 10% by weight of Re on a support selected from the group consisting of graphite, activated carbon, $ZrO_2$, $Al_2O_3$, $SiO_2$ and $TiO_2$,
  a precipitated catalyst comprising from 1 to 90% by weight of Co,
  a precipitated catalyst comprising from 0.5 to 60% by weight of Cu or
  a precipitated catalyst comprising from 15 to 85% by weight of Co and from 5 to 20% by weight of Cu,
where the sum of the contents of Co and Cu does not exceed 100% by weight, is used as fixed-bed catalyst.

10. The process according to claim 1, wherein the mixture (III) is obtained by continuous prehydrogenation of a solution comprising carboxylic acid (I) and water, with the solution having an acid number of from 50 to 900 mg KOH/g.

11. The process according to claim 10, wherein the prehydrogenation is carried out with recirculation and from 50 to 98% by weight of the prehydrogenated solution is recirculated to the prehydrogenation.

* * * * *